(12) United States Patent
Korpas et al.

(10) Patent No.: US 11,160,864 B2
(45) Date of Patent: Nov. 2, 2021

(54) PAIN RELIEF UTILIZING A COMBINATION OF POLYMER BASED MATERIALS

(71) Applicants: E.K. Licensing, LLC, Westland, MI (US); Jack William Shirlin, Garden City, MI (US)

(72) Inventors: Emery Korpas, Westland, MI (US); Jack William Shirlin, Garden City, MI (US)

(73) Assignees: E.K. Licensing, LLC, Plymouth, MI (US); Jack William Shirlin, Garden City, MI (US)

( * ) Notice: Subject to any disclaimer, the term of this patent is extended or adjusted under 35 U.S.C. 154(b) by 0 days.

(21) Appl. No.: 16/779,754

(22) Filed: Feb. 3, 2020

(65) Prior Publication Data

US 2020/0246457 A1 Aug. 6, 2020

Related U.S. Application Data

(62) Division of application No. 15/599,822, filed on May 19, 2017, now Pat. No. 10,548,977.

(60) Provisional application No. 62/339,570, filed on May 20, 2016.

(51) Int. Cl.
| | |
|---|---|
| *A61N 5/06* | (2006.01) |
| *A61K 41/00* | (2020.01) |
| *A43B 17/00* | (2006.01) |
| *A61L 15/24* | (2006.01) |
| *A61L 15/42* | (2006.01) |
| *A61L 15/58* | (2006.01) |
| *A61L 15/18* | (2006.01) |
| *A61K 33/34* | (2006.01) |
| *A61K 33/242* | (2019.01) |
| *A61N 5/067* | (2006.01) |

(52) U.S. Cl.
CPC .......... *A61K 41/0004* (2013.01); *A43B 17/00* (2013.01); *A61K 33/242* (2019.01); *A61K 33/34* (2013.01); *A61L 15/18* (2013.01); *A61L 15/24* (2013.01); *A61L 15/42* (2013.01); *A61L 15/58* (2013.01); *A61N 5/062* (2013.01); *A61L 2420/08* (2013.01); *A61N 5/067* (2021.08)

(58) Field of Classification Search
CPC ...................................................... A61L 15/18
See application file for complete search history.

(56) References Cited

U.S. PATENT DOCUMENTS

| | | | |
|---|---|---|---|
| 4,906,849 | A | 3/1990 | Duo et al. |
| 5,487,739 | A | 1/1996 | Aebischer et al. |
| 6,179,826 | B1 | 1/2001 | Aebischer et al. |
| 6,455,140 | B1 | 9/2002 | Whitney et al. |

(Continued)

FOREIGN PATENT DOCUMENTS

WO WO-2014022049 A1 * 2/2014 ............ G02C 7/10

OTHER PUBLICATIONS

Eccles (The Journal of Alternative and Complementary Medicien, vol. 11, No. 2, A Critical Review of Randomized Controlled Trials of Static Magnets for Pain Relief) (Year: 2005).

*Primary Examiner* — Benjamin J Packard
(74) *Attorney, Agent, or Firm* — Howard & Howard Attorneys PLLC

(57) ABSTRACT

A pain relief device and method or system to aid in the resolution of pain in a body including at least one layer of PVDF film and at least one other layer for directional purposes, as well as a polarizing layer. The device can be packaged in various ways.

15 Claims, 5 Drawing Sheets

(56) References Cited

U.S. PATENT DOCUMENTS

| | | |
|---|---|---|
| 6,475,609 B1 | 11/2002 | Whitney et al. |
| 6,628,989 B1 | 9/2003 | Penner et al. |
| 6,942,634 B2 | 9/2005 | Odland |
| 7,283,874 B2 | 10/2007 | Penner |
| 7,424,325 B2 | 9/2008 | Koller et al. |
| 7,812,025 B2 | 10/2010 | Matsumoto et al. |
| 7,883,535 B2 | 2/2011 | Cantin et al. |
| 7,930,031 B2 | 4/2011 | Penner |
| 7,947,270 B2 | 5/2011 | Franklin |
| 7,951,831 B2 | 5/2011 | Hammock et al. |
| 7,952,349 B2 | 5/2011 | Huang et al. |
| 8,088,163 B1 | 1/2012 | Kleiner |
| 8,277,510 B2 | 10/2012 | Kleiner |
| 8,292,960 B2 | 10/2012 | Kleiner |
| 8,337,485 B2 | 12/2012 | Ludlow et al. |
| 8,343,189 B2 | 1/2013 | Assell et al. |
| 8,343,536 B2 | 1/2013 | Bates et al. |
| 8,557,163 B2 | 10/2013 | Chian et al. |
| 8,574,146 B2 | 11/2013 | Gillespie, Jr. et al. |
| 8,577,460 B2 | 11/2013 | Penner |
| 8,708,701 B2 | 4/2014 | Levens et al. |
| 8,715,355 B2 | 5/2014 | Kleiner |
| 8,721,520 B2 | 5/2014 | Caira et al. |
| 8,758,798 B2 | 6/2014 | Stopek et al. |
| 8,758,799 B2 | 6/2014 | Stopek et al. |
| 8,758,800 B2 | 6/2014 | Stopek et al. |
| 8,808,305 B2 | 8/2014 | Kleiner |
| 8,883,218 B2 | 11/2014 | Radominiska-Pandya et al. |
| 8,896,211 B2 | 11/2014 | Tomer et al. |
| 8,934,972 B2 | 1/2015 | Penner |
| 8,980,302 B2 | 3/2015 | Stopek et al. |
| 9,011,754 B2 | 4/2015 | Leong et al. |
| 9,044,209 B2 | 6/2015 | Dayton et al. |
| 9,044,397 B2 | 6/2015 | Choi et al. |
| 9,050,265 B2 | 6/2015 | Jamison et al. |
| 9,057,068 B1 | 6/2015 | de la Chapelle et al. |
| 9,271,824 B2 | 3/2016 | Ludlow et al. |
| 9,314,618 B2 | 4/2016 | Imran et al. |
| 2004/0011685 A1 | 1/2004 | Lux et al. |

\* cited by examiner

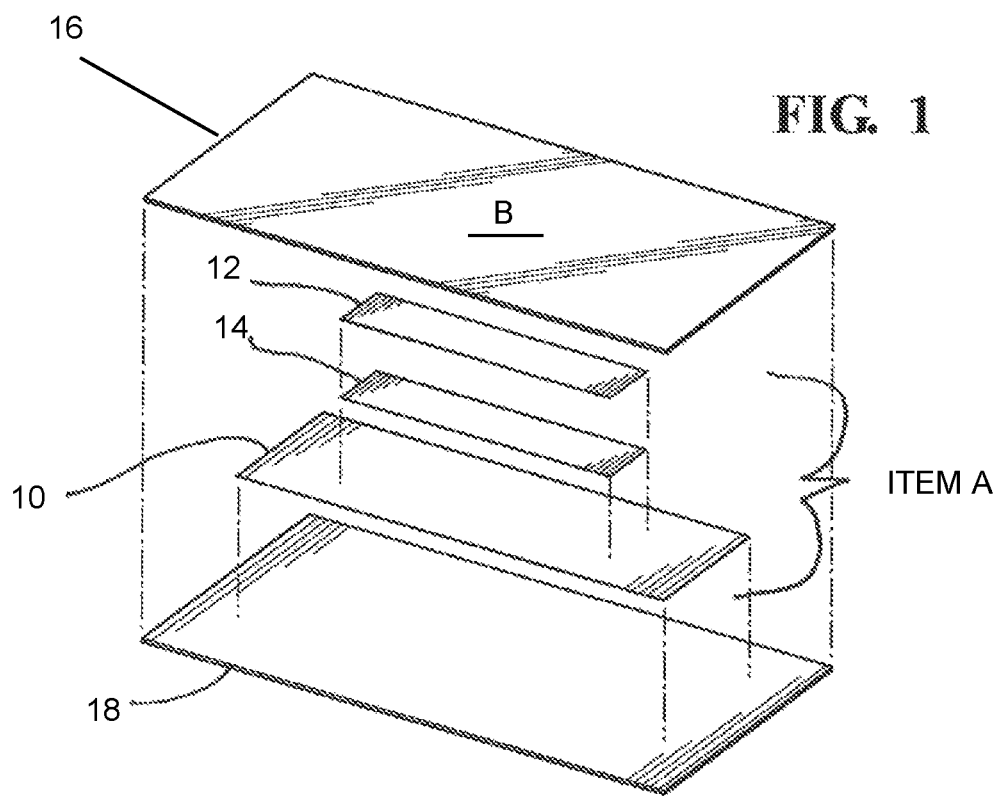
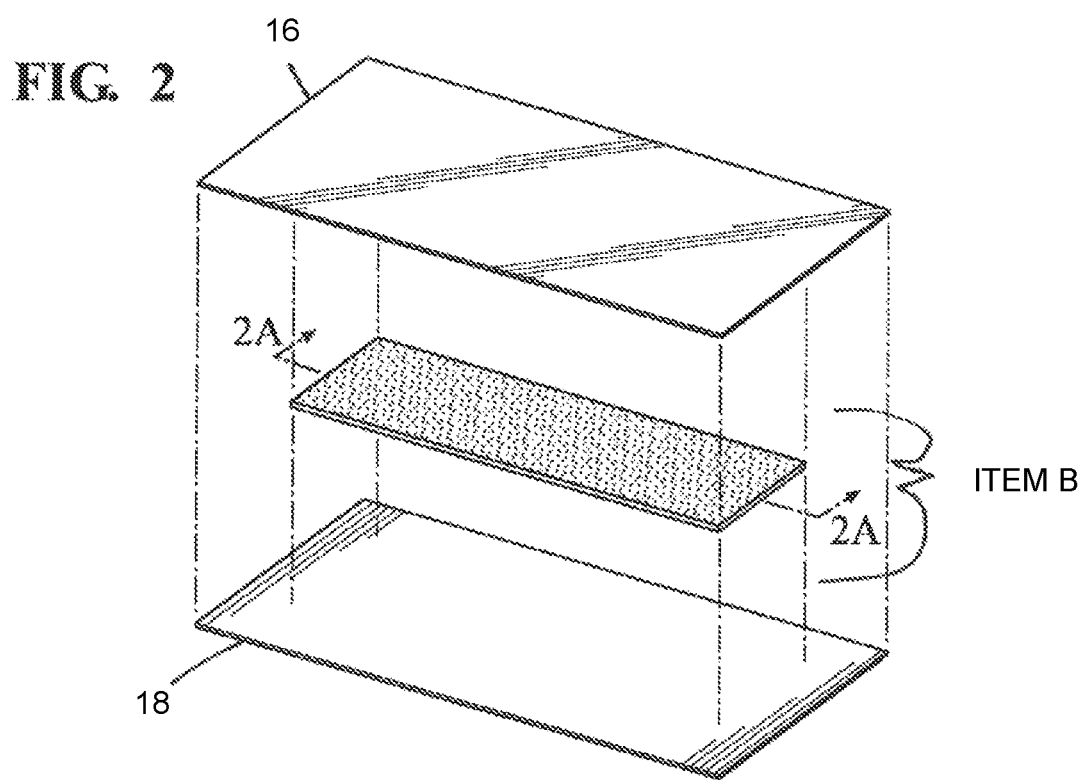

ITEM A OR B

ITEM A OR B

PAIN RELIEF UTILIZING A COMBINATION OF POLYMER BASED MATERIALS

RELATED APPLICATIONS

The subject application is a divisional application of U.S. Nonprovisional patent application Ser. No. 15/599,822 filed on May 19, 2017, which claims priority to and the benefit of U.S. Provisional Patent Application No. 62/339,570, filed on May 20, 2017, the entire contents of which are hereby incorporated by reference.

BACKGROUND OF THE INVENTION

1. Field of the Invention

A pain relief item enclosed by two dissimilar products. The combination is then surrounded by top and bottom cover and when placed near the body will relieve pain.

2. Description of the Prior Art

Pain relief has long been known to be a challenge through-out the world. Many areas of medicine are using chemicals and a diversity of electrical impulse devices. Some others use laser and LED devices. Opioids have become very dangerous to many patients.

There was a demonstration by some scientists who had demonstrated a cross-polymer of sorts which caused pain relief.

PVDF is used in many industries all over the world. The general uses in medicine are limited to Western Blotting. As a membrane, it is used in repair of veins and heart muscle tissue. For example, as a sensor it is used in sleep disorder studies to monitor air flow of patients.

SUMMARY OF INVENTION

There is no device at the present time of a pain relief device which can last a 15-20 year duration without breakdown that is not ingested to be penetrated into the human body. Most interesting with this invention, no direct skin contact is required and most important no wires, no batteries and it is very portable.

The invention uses PVDF film as resonator of low reverberation of the body tissue energy. It is believed that a regeneration of cells occurs, thereby relieving pain.

The materials are combined and packaged in a way as to best utilize the potential of the PVDF film. In this manner a more precise and better pain relief takes place.

The invention is non-invasive to the body and drug free.

Other advantages are that materials can be packaged to meet any configuration other than enclosing it into a metallic seal.

BRIEF DESCRIPTION OF DRAWINGS

Additional advantages of the present invention will be readily appreciated, as the same becomes better understood by reference to the following detailed description when considered in connection with the accompanying drawings wherein:

FIG. 1 is an exploded perspective schematic view of a product having the layers indicated in combination;

FIG. 2 is an exploded perspective schematic view of an alternate version of the product of FIG. 1;

DETAILED DESCRIPTION OF INVENTION

Figure 2A:
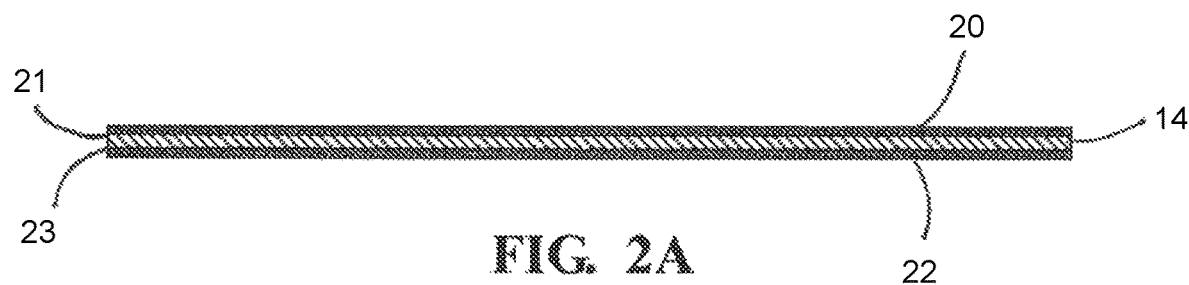
FIG. 2A is a cross-sectional view of the product of FIG. 2 along the line 2A-2A of FIG. 2.

The top and bottom covers can be of any material other than metallic in composition. The invention can be surrounded by laminating or bound in two pieces of sports tape. It may also be incorporated into other wellness products to help accelerate relief or healing.

The copper tape acts as a reflective shield against loss of film activity away from the body. Copper is also an enhancement to the invention in that it is also a generator of resonance.

Copper and silver are both noble metals which both have an extra electron in the outer orbit, thus e-spin/plasmon resonance exists. The latter is the cause of resonance with the body.

The PVDF used in this invention is preferably silver doped.

The polarizer polymer is used to make this resonance more effective when being used.

The total sealing of the copper tape/PVDF film/polarizer become one integrated item. As previously shown the coverings may be made of any material other than metallic materials. The coverings must be less than $\frac{1}{16}$th inch thick. During the process of sealing the temperature must not exceed 130 degrees F. It is preferred that the covering is flexible to conform against the surface of the body to which it is applied, although some stiffness in the credit card sized package is manageable for use in relief of headaches and other inflammatory pain.

The PVDF film is very critical due to its functional properties as related to cellular body tissue.

These properties are as follows:

Frequency: 1-2 Hertz.

Acoustic impedance is the same as human tissue. The physical nature is that it is hydrophobic (stabilizing thermodynamics of nearby H2O molecules) a generator of entropy. The basic nature of PVDF is the sensitivity to low energy changes. i.e. pressure, temperature, vibration and very low level disturbances.

The unique function of PVDF makes it suitable for the purpose of pain relief and possibly long term relief.

Direct skin contact, if available, is probably best, but not required. The field of affect ranges from direct skin contact to approximately $\frac{3}{4}$" to 1" to have positive results based on evidence to date.

Using the item through clothing is fine due to the physical affects which are the nature of the invention, and it is still functional. It is believed that both of the above methods were conclusive as to efficacy with positive results in each.

When the invention is used near the body, cellular frequencies are projected out and PVDF film with high sensitivity becomes more active, thus causing positive frequency feedback.

The frequencies exchanged in this manner signal to the cells which are in dysfunction that there is new energy available to regenerate themselves.

Dr. K. Meyl (THE NEW TESLA) in his analysis of the new physics proves that the energy fields transmitted in nature are scalar waves/vortex. He also proves in biology that this type of energy/frequency is the functional basis of cellular communication.

Scalar waves are a combination of electrical energy and electromagnetic wave propagation.

Based on this new science which has been and is being proven more and more world-wide today, the total functionality of PVDF in the invention is very similar to this physics. Now we can understand why it is effective in human tissue regeneration to help relieve pain.

Once the three components copper tape 10 (¾"×2" as shown), polarizer 12 (⅓"×1¾" as shown), and PVDF film 14 (⅓"×1¾" as shown) are bound together as ITEM A, it may be used in a number of different ways as demonstrated in the following pictures. For all the samples the ITEM A has been ghosted. In actual use the ITEM A is preferred to be enclosed without visual detection such as the cover or enclosure in FIG. 1 which would be non-metallic and have the cover portions 16 and 18 heat sealed or otherwise bonded together.

If the polarizer 12 is disposed on only one side of PVDF film 14, then there will be directionality to the device wherein the side of the device having the polarizer would be the side that would face the body (toward the skin) as set forth in FIG. 1 and the B (body) side. Such directionality would be noted on the packaging for the device to explain to the user that one side of the device faces the body (or skin) and the other side faces away from the body (or skin). It is also anticipated that the device may be manufactured with a PVDF film and polarizer combination on both sides of a copper strip, which would eliminate any need for directionality.

An alternative to ITEM A would be ITEM B as shown in FIGS. 2 and 2A. A strip of PVDF film is dipped on both sides into a bath of polyvinyl alcohol combined with iodine (to cause a polarizing effect) as a polarizing layer 21 and 23 on both sides of the PVDF film 14. Then the PVDF is sprayed with conductive copper to create a layer on both sides 20 and 22 to eliminate the copper tape 10 of ITEM A to create ITEM B. The assembly of the packaging and handling is made that much easier with the combined ITEM B device. Also, ITEM B would not have such a directionality issue, and would work effectively in either direction (on either side) as applied to the body. ITEM B, however, could be sprayed on one side only and provide the same benefits as ITEM A but be directional.

Figure 2B:
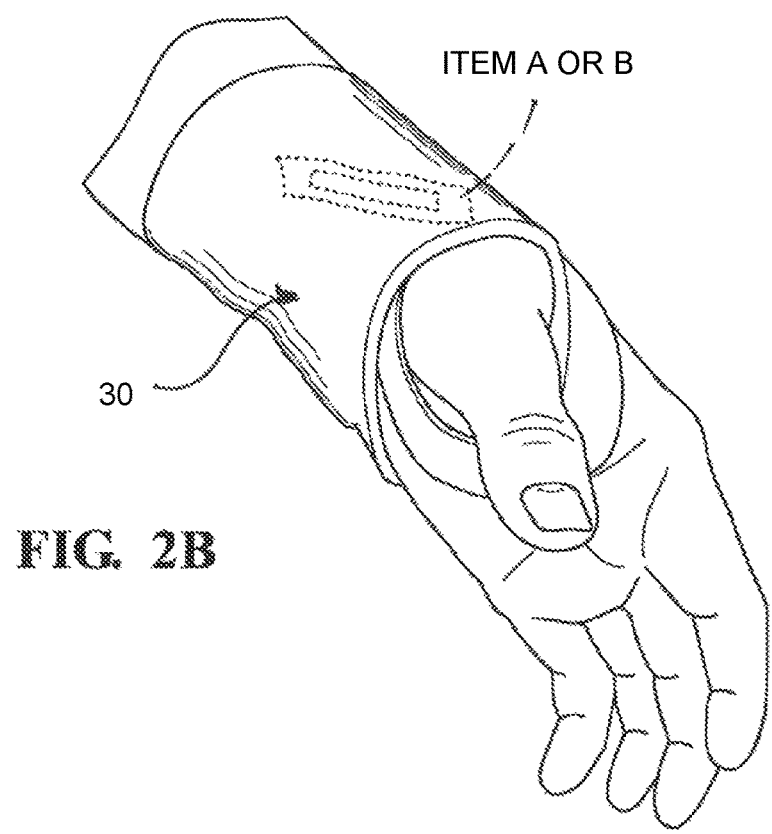
FIGS. 2B, 2C, and 2D illustrate packaging using the invention packaged into a wrist brace, an elbow brace, and a knee brace, respectively.
Figure 2C:
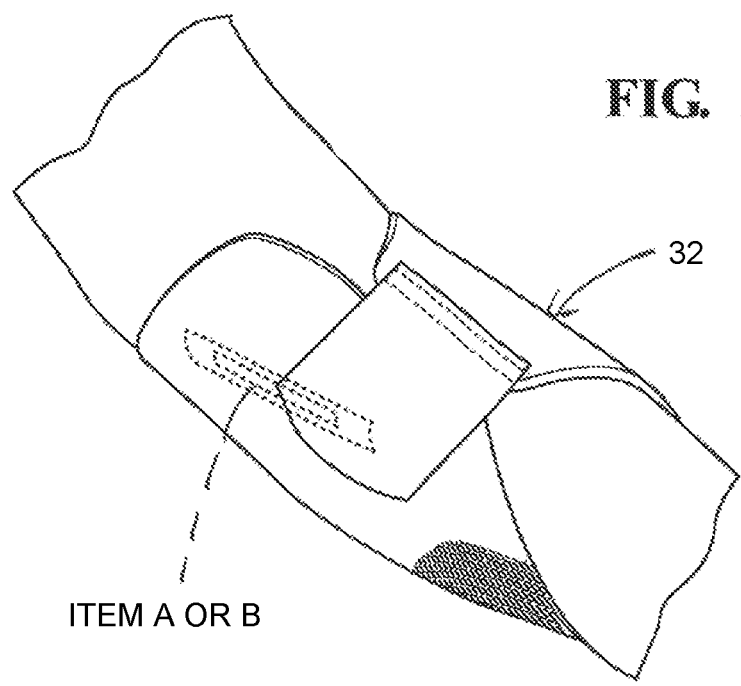
Figure 2D:
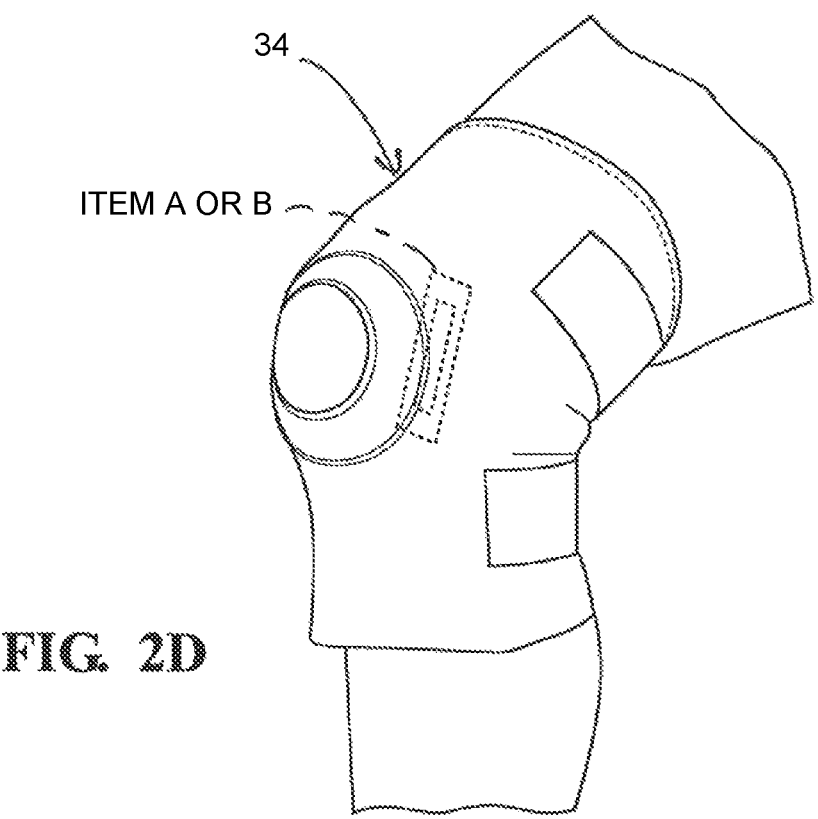

FIGS. 2B, 2C, and 2D demonstrate the application of invention with existing wrist joint wrap 30, elbow joint wrap 32 and knee joint wrap 34. In these images the ITEM A or ITEM B is ghosted and preferably between the wrap and the skin in contact with the skin, but it is not necessary to make contact with the skin, but may be attached on the outside of wrap as deemed necessary (via Velcro packaging, sports tape or some like functional attachment). Based on analysis to date, it is understood that the effectiveness of the invention in this form can occur in a range from at least one-half inch from the outer skin of the body up to contact with the body and through porous material such as a wrap. It is not limited to joints, but, in fact, is believed to be effective in response to any inflammatory pain that the body would express where the acoustic impedance of the device is the same as human tissue (or nerves) that emanate from inflammatory pain. A wrap in the forearm for tennis elbow, a thigh wrap, a calf wrap, an ankle brace, a back wrap, and a myriad of other options exist for placement of the invention on the pain site or at a meridian (as defined in acupuncture and similar disciplines) controlling or otherwise impacting the pain site.

Figure 3A:
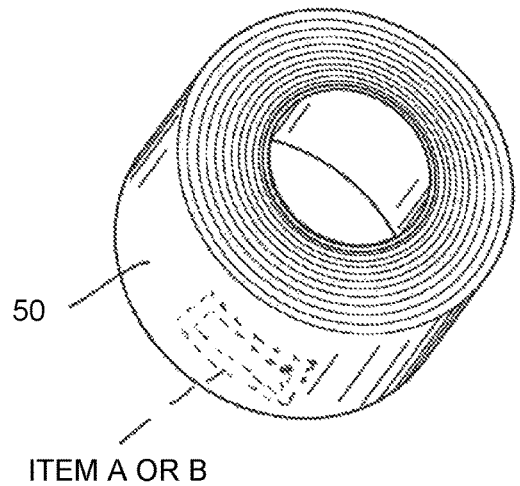
FIGS. 3A and 3B illustrate sports tape incorporating the invention to be placed and adhered as needed or desired on a body.
Figure 3B:
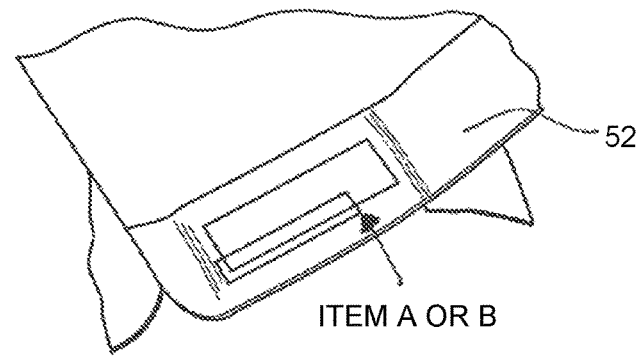
Figure 5:
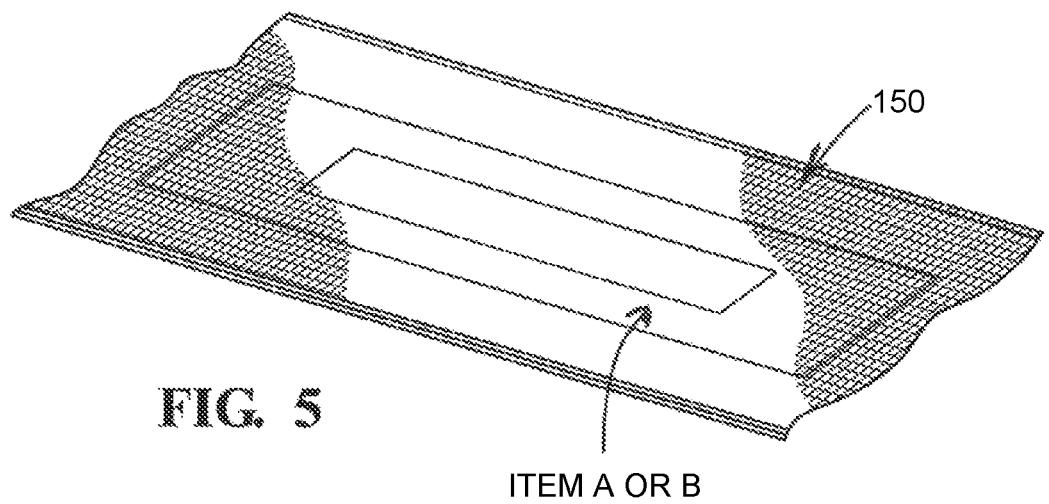
FIG. 5 illustrates another option where the invention is embedded in a KT Tape configuration.

FIGS. 3A, 3B, 3C and 3D demonstrate different configurations of said invention as packaged. FIG. 3A demonstrates that ITEM A or B can be embedded on adhesive tape, such as sports tape 50. Once the ITEM A or ITEM B product is placed on the tape, the tape can then be placed on any part of the body where the pain emanates from, on any pain meridian that would normally be used for acupuncture therapy or even a combination thereof. Another option might be to place the ITEM A or B into the gauze of an adhesive bandage 52 as shown in FIG. 3B to place the invention in the desired location. The invention can also be used effectively with KT Tape such as that supplied by KT Health LLC and shown as 150 in FIG. 5 where ITEM A or ITEM B would be placed between the tape and the skin for specific placement at a source of inflammatory pain as determined by the person or therapist who defines the pain site and enhance whatever therapeutic advantages are supplied by the KT Tape itself.

Figure 3C:
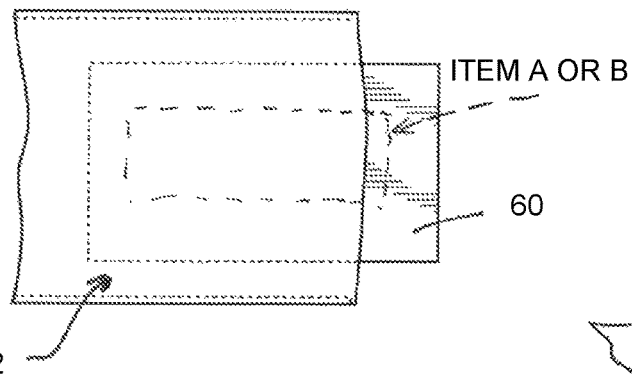
FIG. 3C illustrates a credit card shaped product disposed into a sleeve.

FIG. 3C illustrates that the packaging can include a credit card sized outer layer 60 that could be transported in any sleeve 62 (or wallet) or other location accessible to a user. In this form, it is available to a user at all times. For example, if a user has a headache (migraine or otherwise), the user can take the credit card sized package 60 and apply it by hand to the forehead, back of the neck or other placement in order to obtain temporary pain relief for the headache, which many times also relieves the headache itself. This could be placed via tape or other mechanism to hold it in place. The place of application might also be to the cheek or other area around the mouth (outside of the skin) if there is dental pain that needs to be temporarily alleviated due to some dental incident or dental procedure. A user could also place the credit card sized device 60 within a carrier or package that might already exist near the pain site, such as the portion of a brassiere near the site of some back pain, or a portion of a belt or flexible portion of clothing near a pain site in the abdomen or lower back. Such activity could be used as an alternative to adhesive tape or other attachment devices.

Due to the fact that ITEM A or ITEM B is flexible, it can be used any wellness or therapeutic application where inflammatory pain is involved.

Figure 3D:
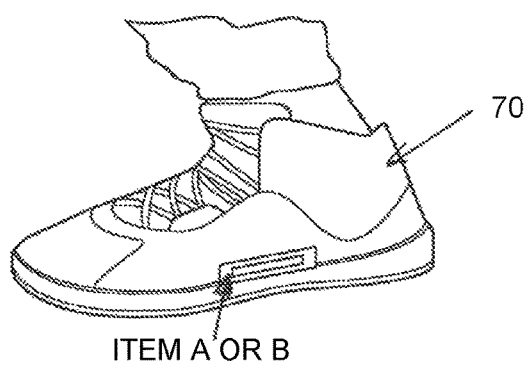
FIGS. 3D and 3E illustrate the use of the invention to relieve foot pain and disposed attached to the outside of a shoe or inserted into the inside of the shoe.
Figure 3E:
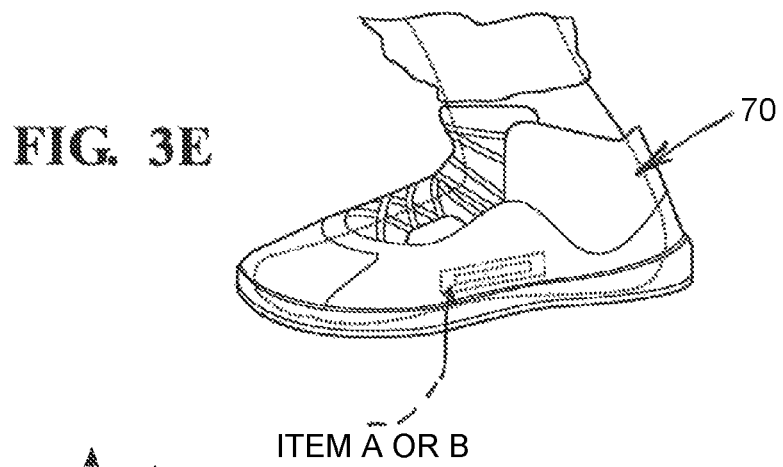

Following examples show our present configuration of ITEM A sealed in a laminate. FIG. 3C illustrates the invention in a credit card sized or smaller package 60 that can be placed in association within a shoe 70 to relieve inflammatory foot pain. The ITEM A or ITEM B can be attached to the outside of the shoe 70 (as shown in FIG. 3D) or can be placed anywhere as selected on the inside of the shoe 70. It may be placed between the shoe 70 and the shoe insole. It may be placed on the insole of the shoe 70 either fixed or loosely held in place by the foot (either with a sock on the foot or sockless).

With new location designs such as pocketing of ITEM A once sealed, we are looking at simple and convenient ways of using this invention.

The device can also improve current items which entail wellness healing.

Figure 4:
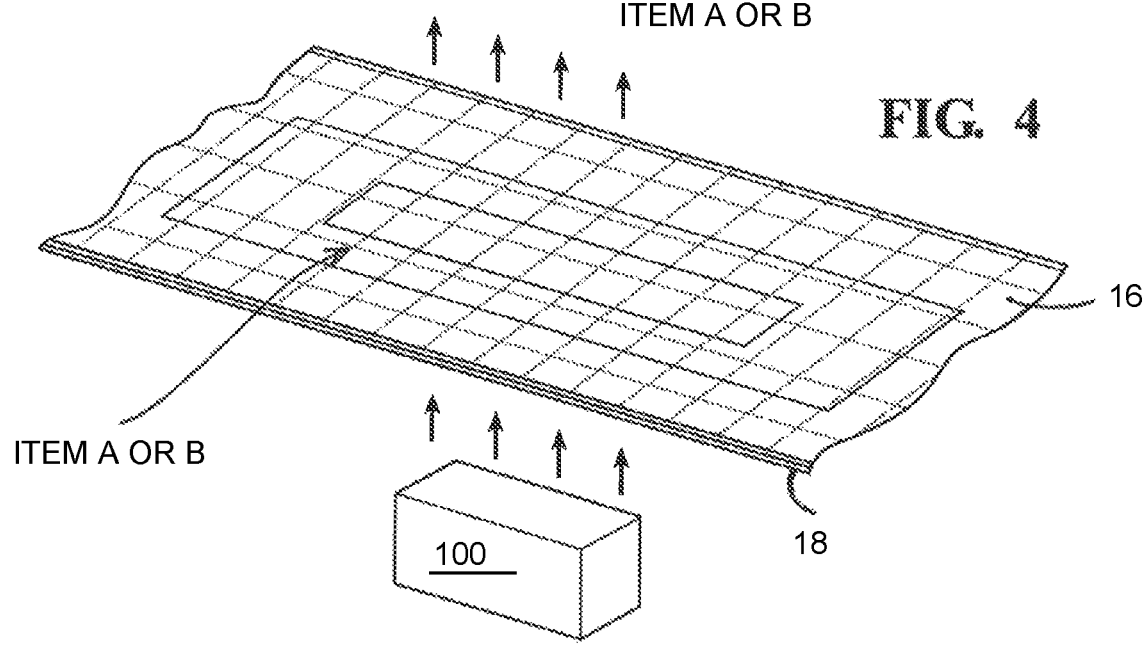
FIG. 4 illustrates the use of the invention with a light therapy device.

With a red laser light therapy product 100, the device of the present invention is able to cut usage times required by manufacturers of red laser therapy devices (pulsed or non-pulsed) down by at least half the amount of time. So half the time is required with ITEM A or ITEM B embedded into or otherwise attached to the light therapy device where the laser is directed through the ITEM A or ITEM B as shown in FIG. 4, where 100 is the source of the laser and the arrows demonstrate the direction of treatment toward the body (or skin). As described here, the ITEM A or ITEM B can be placed in between the red laser light source and the body however the user determines it to be packaged as long as the laser light runs through ITEM A or ITEM B prior to reaching the body (or skin).

In using this invention the time required near body application are as follows: For headaches approximately 30-60 seconds. Other aches use in inflammatory pain area for about 2-5 minutes. More severe inflammatory pain may take 20 to 30 minutes. For continuous use, 6-8 hours may relieve severe pain within this time frame.

Many modifications and variations of the present invention are possible in light of the above teachings. The invention may be practiced otherwise than as specifically described within the scope of the novelty set forth in description of the subject invention.

What is claimed is:

1. A pain relief assembly for pain relief, wherein said assembly comprises:
   a composite comprising:
   a first layer forming a base having a noble metal as an element of the material;
   a second layer disposed on said first layer, wherein said second layer includes a PVDF film;
   a third layer disposed on said second layer including a polarizer; and
   a package containing the composite and configured to be applied to a person's body to relieve pain.

2. The pain relief assembly as set forth in claim 1, wherein said package is a flexible package.

3. The pain relief assembly as set forth in claim 1, wherein said package can be adapted to come into contact with the outer skin.

4. The pain relief assembly as set forth in claim 1, wherein the composite is integrated with a package capable of placing the composite in a location defined by inflammatory pain emanating from a human body.

5. The pain relief assembly as set forth in claim 1, wherein the composite is integrated with a package capable of placing the composite in a location defined by inflammatory pain emanating from an animal.

6. The pain relief assembly as set forth in claim 1, wherein said first layer is sprayed onto said second and third layers.

7. The pain relief assembly as set forth in claim 1, wherein said composite can be associated with a shoe for foot pain.

8. The pain relief assembly as set forth in claim 1, adapted for placement at an acupuncture meridian for treatment.

9. The pain relief assembly as set forth in claim 1, wherein said composite is associated with adhesive film to permit placement wherever needed in response to inflammatory pain.

10. The pain relief assembly as set forth in claim 9, wherein the adhesive is further defined as an adhesive bandage.

11. The pain relief assembly as set forth in claim 1, further comprising a laser light therapy source wherein the laser light is transmitted through said composite into a body.

12. A method of forming a pain relief composite comprising:
    providing a first layer forming a base having a noble metal as an element of the material;
    applying a second layer to said first layer, wherein said second layer includes a PVDF film; and
    applying a third layer to said second layer, wherein said third layer includes including a polarizer; and
    packaging the layers in a package configured to be applied to a person's body at a location defined by inflammatory pain for the purpose of relieving the inflammatory pain.

13. The method as set forth in claim 12, wherein the layers are formed by taking said PVDF layer and dipping it on both sides into a bath of polyvinyl alcohol combined with iodine (to cause a polarizing effect) as a polarizing layer on both sides of the PVDF film layer, then spraying that combination with a conductive noble metal copper to create a layer on at least one side of the combination.

14. The pain relief assembly as set forth in claim 1, wherein the composite is formed by taking said PVDF film and dipping it on both sides into a bath of polyvinyl alcohol combined with iodine to cause a polarizing effect as a polarizing layer on both sides of the PVDF film, then spraying that combination with a conductive noble metal of the first layer to create a layer on at least one side of the combination of the polarizing layer and the PVDF film.

15. The pain relief assembly as set forth in claim 14, wherein said noble metal is sprayed onto said PVDF film.

* * * * *